United States Patent [19]

Motoyama et al.

[11] Patent Number: 4,540,602

[45] Date of Patent: Sep. 10, 1985

[54] PROCESS FOR THE PREPARATION OF ACTIVATED PHARMACEUTICAL COMPOSITIONS

[75] Inventors: Shimesu Motoyama, Asaka; Satoshi Sato, Tokyo; Seiichi Umeda, Tokyo; Huotsune Yasumi, Tokyo; Emiko Sudo, Tokyo; Yuko Takasaka, Tokyo; Takuichi Tsujino, Tokyo, all of Japan

[73] Assignee: Freund Industry Company, Limited, Tokyo, Japan

[21] Appl. No.: 420,384

[22] Filed: Sep. 20, 1982

Related U.S. Application Data

[63] Continuation of Ser. No. 139,750, Apr. 14, 1980, abandoned.

[30] Foreign Application Priority Data

Apr. 13, 1979 [JP] Japan .................................. 54-44261
Jun. 16, 1979 [JP] Japan .................................. 54-75774
Jun. 17, 1979 [JP] Japan .................................. 54-76203

[51] Int. Cl.³ .......................... B01J 13/02; A61K 9/50
[52] U.S. Cl. .......................... 427/213.31; 252/363.5; 424/33; 424/34; 424/35; 424/37; 427/3; 427/213.35; 427/213.36
[58] Field of Search ............... 424/35, 34; 427/213.31, 427/213.36, 3, 213.35

[56] References Cited

U.S. PATENT DOCUMENTS

| | | |
|---|---|---|
| 2,650,895 | 9/1953 | Wallenmeyer et al. .............. 424/34 |
| 2,805,977 | 9/1957 | Robinson et al. ................. 424/35 X |
| 2,875,130 | 2/1959 | Grass, Jr. et al. ...................... 424/19 |
| 2,897,119 | 7/1959 | Dunn ....................................... 424/34 |
| 3,056,728 | 10/1962 | Ohtaki ............................... 424/34 X |
| 3,445,563 | 5/1969 | Clegg et al. ........................... 424/35 |
| 3,493,652 | 2/1970 | Hartman ........................... 424/35 X |
| 3,565,559 | 2/1971 | Sato et al. ............................. 424/37 |
| 3,577,514 | 5/1971 | Robinson ............................... 424/22 |
| 3,594,326 | 7/1971 | Himmel .......................... 427/213.32 |
| 3,691,090 | 9/1972 | Kitajima et al. ............... 427/213.36 |
| 3,960,757 | 6/1976 | Morishita et al. ............... 427/213.36 |

Primary Examiner—Richard D. Lovering
Attorney, Agent, or Firm—Oblon, Fisher, Spivak, McClelland & Maier

[57] ABSTRACT

Disclosed is a process for the preparation of an activated pharmaceutical composition containing a solid drug that is scarcely soluble in water, the pharmaceutical composition being characterized in that, when it is administered orally, the drug is readily absorbed to attain its high blood concentration quickly. This process is carried out by providing a solid drug that is scarcely soluble in water, dispersing the drug in water in the presence of a water-soluble high-molecular substance to form a disperse system containing the drug in the form of finely divided particles substantially not greater than 10μ in diameter, and then removing the water from the disperse system.

10 Claims, 9 Drawing Figures

PROCESS FOR THE PREPARATION OF ACTIVATED PHARMACEUTICAL COMPOSITIONS

This application is a continuation of application Ser. No. 139,750 filed Apr. 14, 1980, now abandoned.

BACKGROUND OF THE INVENTION

This invention relates to a process for the preparation of activated pharmaceutical compositions which have a high degree of bioavailability because of their good absorbability in the digestive tract. The field of art to which this invention pertains belongs to class 424 of the U.S. patent classification.

One prior art process for the preparation of a pharmaceutical composition is disclosed in Japanese Patent Publication No. 5798/1960. This process comprises adding Carbowax to chloroamphenicol palmitate, dissolving this mixture in a hot hydrophilic organic solvent, and then cooling the resulting solution rapidly to obtain a finely divided amorphous form of chloramphenicol palmitate. However, the composition prepared by this process has poor redispersibility in water because it contains Carbowax having a low melting point.

Another prior art process for the preparation of a pharmaceutical composition is disclosed in Japanese Patent Layed Open No. 2316/1979. This process comprises providing a blend of nifedipine, a first additive selected from glycerol, vegetable oils, and the like, and a second additive selected from polyvinyl pyrrolidone, methyl cellulose, hydroxypropyl cellulose, and the like; dissolving this blend in an organic solvent; and then removing the organic solvent from the resulting solution. However, this process has the disadvantage that the use of large amounts of organic solvent involves a great risk.

An organic solvent is used as the solvent in both of the above-described processes. In this respect, they are distinguished from the process of the present invention in which water is used as the dispersion medium.

In addition, an art analogous to the present invention is found in Japanese Patent Publication No. 42390/1971. Specifically, there is disclosed a process for the preparation of a suspension of chloramphenicol palmitate that is scarcely soluble in water, which comprises melting a mixture of chloramphenicol palmitate and a surface-active agent and then grinding this melt in an aqueous solution of a water-soluble high-molecular substance (e.g., methyl cellulose) by means of a colloid mill. However, the chloramphenicol palmitate included in the melt may be closely combined with the surface-active agent and be different from chloramphenicol palmitate itself. Moreover, this analogous art is directed to the preparation of suspensions. Thus, the novelty of the present invention is not denied by this analogous art.

Another art analogous to the present invention is found in Japanese Patent Publication No. 33676/1970. This relates to a process for the preparation of a finely divided suspention of an organic acid ester of chloramphenicol that is scarcely soluble in water, which comprises melting a mixture of the organic acid ester of chloramphenicol and a surface-active agent, dispersing this melt in warm water, and then cooling the resulting aqueous dispersion to precipitate the organic acid ester of chloramphenicol in the presence of, for example, polyvinyl alcohol. Again, a mixed melt of an organic acid ester of chloramphenicol and a surface-active agent is used in this process. However, the organic acid ester of chloramphenicol included therein may be closely combined with the surface-active agent to form a substance different from the organic acid ester of chloramphenicol itself. Moreover, it is certain that the formation of micelles of the surface-active agent occurs in the suspension prepared by this process, as contrasted with the process of the present invention in which no micelle formation is recognized. Furthermore, this analogous art is also directed merely to the preparation of suspensions. Thus, the novelty of the present invention is not denied by this analogous art, either.

BRIEF SUMMARY OF THE INVENTION

It is the primary object of the present invention to provide a novel process for the preparation of an activated pharmaceutical composition containing a solid drug that is scarcely soluble in water, the pharmaceutical composition being characterized by good redispersibility in water and a high degree of bioavailability.

Briefly stated, in accordance with the present invention, a solid drug that is scarcely soluble in water is dispersed in water in the presence of a water-soluble high-molecular substance to form a disperse system containing the drug in the form of finely divided particles substantially not greater than $10\mu$ in diameter, and the dispersion medium is then removed from the disperse system, whereby a pharmaceutical composition consisting of the finely divided drug coated with the water-soluble high-molecular substance is obtained.

If the water-soluble high-molecular substance has thermally gelling properties, the process of the present invention can be carried out in the following way: A solid drug that is scarcely soluble in water is dispersed in an aqueous solution of the water-soluble high-molecular substance to form a disperse system containing the drug in the form of finely divided particles substantially not greater than $10\mu$ in diameter, and this disperse system is heated to effect gelation of the water-soluble high-molecular substance. The gel so formed, together with the finely divided drug occluded therein, is separated from the liquid phase and then dried. This can greatly save the cost required for the removal of the solvent.

In carrying out the process of the present invention, there are a number of procedures for dispersing the drug in water to form a disperse system containing the drug in the form of finely divided particles.

According to a first procedure applicable to the case in which the drug is soluble in aqueous alkaline solutions, the drug is dissolved in an aqueous alkaline solution, and the resulting solution is then neutralized with an acid to precipitate the drug.

According to a second procedure applicable to the case in which the drug is soluble in aqueous acid solutions, the drug is dissolved in an aqueous acid solution, and the resulting solution is then neutralized to precipitate the drug.

According to a third procedure applicable to the case in which the drug is soluble in hydrophobic organic solvents, the drug is dissolved in a hydrophobic organic solvent, and the resulting solution is emulsified in water.

According to a fourth procedure, the drug is pulverized in water.

DETAILED DESCRIPTION OF THE INVENTION

Figure 1:
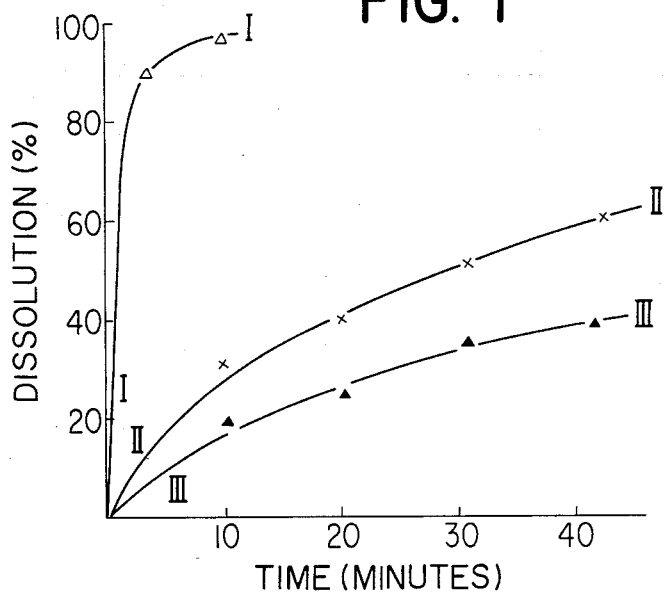
FIG. 1 is a diagram illustrating the results of the dissolution test performed in Example 1.

The term "activated pharmaceutical composition" means a pharmaceutical composition containing a drug which is finely divided, rendered easily redispersible, and hence capable of being readily absorbed.

As described above, the primary object of the present invention is to provide a novel process for the preparation of an activated pharmaceutical composition which exhibits good redispersibility in the digestive tract.

It has been recognized that the value of a drug which is scarcely soluble in water is not only determined by the pharmacological effect of the drug itself, but greatly influenced by the physical properties (particularly, particle size) imparted thereto during the manufacturing process. Accordingly, the method of making finely divided drugs has been studied extensively. Such studies are directed especially to the preparation of finely powdered organic acid salts of chloramphenicol, and a large number of inventions concerned therewith have been disclosed, for example, in Japanese Patent Publication Nos. 5798/1960, 33676/1970, 15286/1971, 17153/1971, 21671/1971, 42390/1971, and the like.

In accordance with the present invention, a solid drug that is scarcely soluble in water is dispersed in water in the presence of a water-soluble high-molecular substance to form a disperse system containing the drug in the form of finely divided particles substantially not greater than $10\mu$ in diameter, and the dispersion medium is then removed from the disperse system, whereby a pharmaceutical composition consisting of the finely divided drug coated with the water-soluble high-molecular substance is obtained.

The water-soluble high-molecular substance used in the process of the present invention may be one having thermally gelling properties. In this case, the aqueous dispersion obtained by dispersing the drug in water is heated to effect gelation of the water-soluble high-molecular substance. The gel so formed, together with the finely divided drug occluded therein, is isolated from the aqueous phase and then dried. This can preferably save the heat energy required for the removal of the solvent.

As stated before, there are a total of 4 procedures by which a solid drug that is scarcely soluble in water is dispersed in water to form an aqueous dispersion of the finely divided drug.

In the prior art, there has been proposed a process for the emulsification of a low-melting drug, such as a fatty acid ester of chloramphenicol, which comprises melting the drug by application of heat and then subjecting the molten drug to mechanical agitation or shearing. However, the molten drug has such a high viscosity that it hardly undergoes a shearing action and hence fails to show a sufficient degree of particle size reduction. Thus, the particle diameter achieved by this process is of the order of $10\mu$ or greater in most cases.

It is also a common practice to carry out the emulsification with the aid of a surface-active agent. The surface-active agents which are suitable for this purpose include, for example, Japanese pharmacopoeial polysorbate 80 that is authorized to be usable in pharmaceutical preparations and has strong emulsifying and solubilizing powder; and HCO-60 that is an addition polymerization product of hydrogenated castor oil with ethylene oxide. These nonionic surface-active agents are being widely used owing to their little interaction with the drug and their lack of taste and odor.

However, it has recently been recognized that the use of a surface-active agent for the purpose of emulsification poses the problem of hemolysis. It has also been reported that, although a drug certainly undergoes a high degree of particle size reduction by using a surface-active agent in appropriate amounts and exhibits a high dissolution rate in in vitro tests or dissolution tests, the in vivo administration of the drug to human beings does not always exhibit an increase in bioavailability or absorbability and even shows a decrease in the area under the blood concentration curve (AUC). The reason for this is considered to be that the finely divided drug is incorporated into micelles of the surface-active agent and, therefore, the absorption thereof is suppressed to reduce the distribution ratio for lipid.

In addition, chloramphenicol fatty acid esters, barbiturates, sulfnilamide, steroids (e.g., cortisone acetate and methylprednisolone), riboflavin, ubidecarenone, and the like are known to be polymorphic. That is, their absorbability varies according to the crystal form and its stability, crystal phase transition, and the like. Accordingly, in the preparation of activated pharmaceutical compositions having a high degree of bioavailability, due consideration should be taken of this problem. In fact, not a few of the drugs which can be used in the process of the present invention exhibit polymorphism.

It is generally known that, as the particle size of a drug decreases, its surface area increases and, therefore, its absorption into a body becomes quicker. However, even if a solid drug that is scarcely soluble in water is formed into finely divided primary particles, a subsequent step of making it into subtle granules, granules, tablets, or other pharmaceutical forms causes the primary particles to cohere. Upon administration, therefore, the primary particles often fail to be redispersed in the digestive tract and thus behave as coarse particles. As a result, the drug tends to be incapable of being easily absorbed into the body.

Paying attention to the relationship between the gastric emptying time and the particle diameter of a drug, the present inventors made a series of experiments in which a slurry of finely divided barium sulfate in water and several solid preparations of finely divided barium sulfate were orally administered to human subjects and their passage through the stomach and the intestine was observed by roentgenography. Thus, it was found that the slurry of finely divided barium sulfate rapidly migrated to the intestine without regard to the presence or absence of gastric contents, while the subtle granules, granules, and tablets formed of finely divided barium sulfate stayed in the stomach for a long time and were slow to migrate to the intestine. Although a part of the drug is absorbed in the stomach, most of it is absorbed in the upper portion or the whole of the small intestine having the largest surface area. Accordingly, it is of critical importance to allow the orally administered drug to migrate through the stomach to the small intestine as rapidly as possible. In the case of a drug for oral use, therefore, the time taken for the drug to migrate to the small intestine (as the site of absorption having the largest surface area) without regard to the presence or absence of gastric contents is the first of the factors determining the bioavailability of the drug.

The drug which has reached the site of absorption as described above passes across the intestinal mucosa. On that occasion, some drugs are absorbed by passive transport and others by active transport, depending on the pharmacological and physicochemical properties of the particular drug. In any case, the essential requirements for every drug that is scarcely soluble in water are that the drug is dispersible in the form of finely divided particles at the site of absorption and that those particles are lipophilic from the viewpoint of distribution ratio.

As stated before, a large number of studies on the particle size reduction of solid drugs have been published, but the particle diameters discussed therein are of the order of several ten microns. According to the above-described experiments of the present inventors, the particle diameter of a drug should be at most $10\mu$ and preferably not greater than $0.5\mu$ in order to allow the drug to migrate through the stomach to the small intestine rapidly without regard to the presence or absence of gastric contents. Since most of the solid drug that are scarcely soluble in water are considered to be absorbed through the lipoid routes of the intestinal mucosa, it is most preferable to disperse the drug in the form of submicron particles (i.e. the so-called colloidal particles) not greater than $0.5\mu$ in diameter.

It has been confirmed that, when the process of the present invention is carried out especially according to the third procedure in which a solid drug that is scarcely soluble in water is dissolved in a hydrophobic organic solvent and the resulting solution is emulsified in water in the presence of a water-soluble high-molecular substance, the particle diameter (as measured by electron microscopy) of the drug redispersed in the digestive tract can be reduced to the order of $0.5\mu$ by selecting a suitable hydrophobic organic solvent and properly controlling the concentration of the drug in the hydrophobic organic solvent.

Judging from the size of the pores of the intestinal mucosa, it seems probable that such submicron drug particles present in the pharmaceutical composition thus obtained are absorbed not by way of the aqueous phase, but directly through the lipoid routes of the intestinal mucosa.

The drug present in the activated pharmaceutical composition prepared by the process of the present invention has such good redispersibility that, after oral administration, it is rapidly carried to the small intestine and readily absorbed into the blood to raise its blood concentration quickly.

Specific examples of the water-soluble high-molecular substance used in the process of the invention include cellulose derivatives such as hydroxypropyl cellulose, methyl cellulose, hydroxyethyl cellulose, hydroxypropyl methylcellulose, hydroxypropyl ethylcellulose, carboxymethyl cellulose sodium salt, and the like; and other polymeric substances such as $\alpha$-starch, hydroxypropyl starch, pullulan, gum arabic, tragacanth gum, gelatin, polyvinyl alcohol, polyvinyl pyrrolidone, and the like. Among these water-soluble high-molecular substances, hydroxypropyl cellulose, methyl cellulose, hydroxypropyl methylcellulose, hydroxypropyl ethylcellulose, hydroxypropyl amylose, hydroxypropyl pullulan, and the like have thermally gelling properties. The foregoing water-soluble high-molecular substances may be used alone or in combination.

The use of water-soluble high-molecular substances, such as Carbowax, having a low melting point (of 100° C. or below) is undesirable because the resulting pharmaceutical composition has poor redispersibility.

Now, the process of the present invention is specifically described with reference to the first procedure in which a solid drug that is scarcely soluble in water is dissolved in an aqueous alkaline solution and the resulting solution is then neutralized with an acid to form an aqueous dispersion of the drug. The following desription applies to the case in which the water-soluble high-molecular substance used does not have thermally gelling properties.

A drug (e.g. phenytoin) that is a solid at ordinary temperatures, scarcely soluble in water, and soluble in aqueous alkaline solutions is dissolved in an aqueous alkaline solution containing gum arabic. To the resulting solution is added an acid, with stirring, so as to neutralize the solution and thereby precipitate the drug in the form of finely divided particles. The aqueous dispersion so formed is spray-dried to obtain an activated pharmaceutical composition having good redispersibility in water. For example, when phenytoin is used as the drug, the pharmaceutical composition thus obtained consists of phenytoin and gum arabic, the finely divided particles of the former being coated with the latter.

In place of the spray drying, the aforesaid aqueous dispersion may be directly granulated by spraying it onto an excipient (e.g. lactose, starch, microcrystalline cellulose, light silicon dioxide, or the like) in a fluid-bed spray granulator.

The second procedure applicble to the case in which a solid drug that is scarcely soluble in water is soluble in aqueous acid solutions is the same as the above-described first procedure, except that the drug is dissolved in an aqueous acid solution and the resulting solution is neutralized with an alkali.

Specific examples of the solid drug that is scarcely soluble in water and is soluble in aqueous alkaline solutions include iopanoic acid, iothalamic acid, indomethacin, nalidixic acid, trichloromethiazide, barbital, hydrochlorothiazide, phenytoin, phenylbutazone, phenobarbital, furosemide, dehydrocholic acid, propylthiouracil, methylthiouracil, methotrexate, folic acid, iodamide, riboflavin, and the like.

Specific examples of the solid drug that is scarcely soluble in water and is soluble in aqueous acid solutions include ethyl aminobenzoate, ethionamide, ajmaline, sulfamethoxazole, sulfamonomethoxin, sulfisoxazole, tetracycline, 1-tryptophan, perphenazine maleate, norepinephrine, methyldopa, levodopa, and the like.

In the above-described first and second procedures which involve the step of neutralizing a solution of a drug to form an aqueous dispersion of finely divided drug, a water-soluble high-molecular substance (e.g. hydroxypropyl cellulose) having thermally gelling properties may be used. In this case, the process of the present invention can be carried out in the following way:

A drug that is a solid at ordinary temperatures, scarcely soluble in water, and soluble in aqueous alkaline solutions is dissolved in an aqueous alkaline solution. Then, a thermally-gelling water-soluble high-molecular substance (e.g. hydroxypropyl cellulose having a gelation temperature of 60° C.) is added to this solution, which is stirred until the hydroxypropyl cellulose is completely dissolved therein. To the resulting solution is added an acid, with stirring, so as to neutralize the solution and thereby precipitate the drug in the form of finely divided particles. Subsequently, the resulting aqueous dispersion is heated at a temperature of 80° C. or above to effect gelation of the hydroxypropyl cellulose. The gel so form, together with the finely divided drug occluded therein, is separated by filtration, washed with warm water at 80° C. or above to remove the salt formed by the aforesaid neutralization, and then dried. Although the drug is in the form of finely divided particles, they are occluded in the gel of the water-soluble high-molecular substance and, therefore, are readily filtered without clogging the filter medium.

In the case of a drug that is soluble in aqueous acid solutions, a thermally-gelling water-soluble high-molecular substance may also be used in the same manner as described above, except that the resulting solution is neutralized with an alkali.

Generally, when finely divided particles of a drug precipitated from its solution, the smaller particles diminish and the larger ones grow as time goes on. However, in the pharmaceutical composition prepared by the process of the present invention, the finely divided particles of the drug are coated with the water-soluble high-molecular substance. Accordingly, no particle growth is observed and the drug is very stably maintained in the finely divided state. This constitutes an outstanding feature of the present invention.

Next, the present process for the preparation of an activated pharmaceutical composition is specifically described with reference to the third procedure in which a solid drug that is scarcely soluble in water is dissolved in a hydrophobic organic solvent, the resulting solution is emulsified in water in the presence of a water-soluble high-molecular substance, and the solvents are then removed from the resulting emulsion.

In this procedure, the solvents (water and organic solvent) of the emulsion may be removed by any suitable drying technique. However, drying techniques such as spray drying and fluid-bed spray granulation are preferred in order to allow the solvents to be evaporated as rapidly as possible. As soon as the solvents are removed, the finely divided particles of the drug are coated with the water-soluble high-molecular substance, so that they neither agglomerate into a mass nor grow to coarse grains. Moreover, upon introduction into water, the water-soluble high-molecular substance dissolves in the water to allow the drug to be easily redispersed in the water.

As described above, an organic solvent solution of the drug is emulsified in water in the presence of a water-soluble high-molecular substance. This means that the water-soluble high-molecular substance may be present in the water or the organic solvent solution or may be added at the time of emulsification.

In the above-described third procedure, a water-soluble high-molecular substance having thermally gelling properties may be used in order to utilize the gelation phenomenon.

Specifically, using a thermally-gelling water-soluble high-molecular substance, an emulsion is prepared in the same manner as described above. Then, this emulsion is heated to effect gelation of the water-soluble high-molecular substance. Usually, it is preferable that the heating temperature is 80° C. or above so as to ensure occurrence of the gelation. The gel so formed, together with the colloidally dispersed organic solvent solution, settles down or floats off and thus parts from the aqueous phase. This gel is separated by filtration or other suitable techniques and then dried to obtain an activated pharmaceutical composition.

The separated gel may be dried either by vacuum-drying it while being kept at the gelation temperature or by cooling it to room temperature and then spray-drying it. In either case, the finely dispersed state of the organic solvent solution in the water is maintained throughout the drying step.

Again in the third procedure involving a gelation step, the finely divided particles of the drug are coated with the water-soluble high-molecular substance as soon as the former is precipitated. As a result, they neither agglomerate into a mass nor grow to coarse grains. The third procedure involving a gelation step is advantageous in that the gel can be readily separated from the liquid phase and, therefore, the heat energy required for the removal of the solvents can be saved.

The hydrophobic organic solvent used in the third procedure may be any organic solvent that, when mixed with water, parts from the water and forms a separate layer. Among others, low-boil organic solvents such as chloroform, methylene chloride, trichloroethylene, trichloroethane, carbon tetrachloride, benzine, n-hexane, benzene, toluene, xylene, ethyl ether, isopropyl ether, methyl ethyl ketone, ethyl acetate, and the like are preferred because they can be readily evaporated during the drying step.

In order to improve the dissolving power of the hydrophobic organic solvent and/or facilitate the emulsification of the organic solvent solution, one or more hydrophilic organic solvents such as ethanol, isopropyl alcohol, acetone, and the like may be added to the aforesaid hydrophobic organic solvent.

The aforesaid hydrophobic organic solvent may also be a nonvolatile oily substance that remains after the drying step and can be orally administered without any harmful effect. Specific examples of the nonvolatile oily substance include glycerides, liquid paraffin, squalane, squalene, lecithin, pristane, low-HLB sorbitan fatty acid esters, low-HLB sucrose fatty acid esters, and the like. It is generally known that a drug is more easily soluble and absorbable in the amorphous state than in the crystalline state. It is one of the outstanding features of the third procedure that, especially if the drug used in the process of the present invention is polymorphic, the amorphous or non-crystalline state thereof can be readily created either by using such a nonvolatile oily substance as the hydrophobic organic solvent or by adding such a nonvolatile oily substance to the aforesaid low-boiling hydrophobic organic solvent. Even if the drug is not polymorphic, such a measure serves to modify the distribution ratio of the drug and thereby enhance the bioavailability thereof.

In carrying out the process of the present invention according to the third procedure in which a solid drug that is scarcely soluble in water is dissolved in a hydrophobic organic solvent and the resulting solution is emulsified in water in the presence of a water-soluble high-molecular substance, the water-soluble high-molecular substance is preferably used in an amount of not less than 5% by weight based on the weight of the water. If necessary, one or more excipients such as starch, lactose, mannitol, powdered cellulose, silicon dioxide, and the like may be added to the water, depending on the pharmaceutical form, dosage, and other factors.

The hydrophobic organic solvent may be used in an amount which allows the drug to be dissolved therein or uniformly dispersed therein in a colloidal state. If a low-boiling hydrophobic organic solvent which will be evaporated during the drying step is used, it is preferable to dilute the drug several times to several ten times because the diameter of the drug particles present in the resulting pharmaceutical composition becomes satisfactorily small. Usually, the drug can be formed into finely divided particles not greater than $1\mu$ in diameter by dissolving one part by weight of the drug in at least one part by weight and preferably 5 to 20 parts by weight of the hydrophobic organic solvent.

According to the above-described third procesure, the process of the present invention can essentially be carried out without the aid of a surface-active agent. However, a small amount of a surface-active agent may be added in order to allow the drug to be easily wetted and dispersed in the digestive tract. For this purpose, dioctyl sodium sulfosuccinate (DOSS), sucrose fatty acid esters, and the like are used because of their lack of hemolytic effect.

Specific examples of the solid drug that is scarcely soluble in water and is soluble in hydrophobic organic solvents include ajmaline, isopropylantipyrine, quinine ethylsulfate, ethenzamide, erythromycin, erythromycin fatty acid esters, kitasamycin, chlorpropamide, chlormezanone, cortisone acetate, diazepam, digitoxin, cyclophosphamide, spironolactone, nalidixic acid, amobarbital, indomethacin, josamycin, nifedipine, ubidecarenone, chloramphenicol palmitate, and the like.

Finally, the present process for the preparation of an activated pharmaceutical composition is specifically described with reference to the fourth procedure in which a solid drug that is scarcely soluble in water is pulverized in an aqueous solution of a water-soluble high-molecular substance and the water is then removed from the resulting aqueous dispersion.

An aqueous solution of a water-soluble high-molecular substance is used in this procedure. However, a hydrophilic organic solvent may be added to the solution, so long as the water-soluble high-molecular substance does not precipitate out. For example, methanol, ethanol, isopropyl alcohol, acetone, and the like can be used for this purpose. The addition of a hydrophilic organic solvent has the effect of accelerating the drying step and, in the case of certain drugs, the effect of enhancing the degree of particle size reduction.

If the water-soluble high-molecular substance is soluble in an organic solvent and the solid drug that is scarcely soluble in water is substantially insoluble in the organic solvent, the present process for the preparation of an activated pharmaceutical composition may also be carried out by pulverizing the drug in a solution of the water-soluble high-molecular substance in the organic solvent and the organic solvent is then removed from the resulting dispersion.

The pulverizer which is used to pulverize the drug may be any suitble type of wet-grinding machine, such as ball mill, vibration mill, Attritor ®, (Union Process Inc.), Polytron ® (Kinematica GmbH, Switzerland), or the like. Using such a wet-grinding machine, the drug is pulverized in an aqueous solution of a water-soluble high-molecular substance. Since wet-grinding machines hve stronger pulverizing power than dry-grinding machines, an aqueous dispersion of a sufficiently fine particles can be obtained. However, it is more preferable to preliminarily dry-grind the drug in advance of the wet-grinding step. The use of a drug having subjected to such a preliminary dry-grinding step is desirable because the subsequent wet grinding step can be carried out smoothly. As a result of the wet-grinding step, the drug is formed into finely divided particles substantially ranging from $0.5\mu$ or less to $5\mu$ in diameter.

The resulting aqueous dispersion of the finely divided drug is preferably dried by means of a spray dryer. Alternatively, the dispersion may be dried by spraying it onto an excipient (e.g. lactose, starch, microcrystalline cellulose, colloidal silicon dioxide, or the like) in a fluid-bed spray granulator.

According to the fourth procedure, the drug may also be pulverized in an aqueous solution of a water-soluble high-molecular substance having thermally gelling properties. In this case, the resulting aqueous dispersion of the finely divided drug is heated to effect gelation of the water-soluble high-molecular substance. The heating temperature need only be high enough for the gelation and generally ranges from 80° to 90° C. The gel so formed, together with the finely divided drug occluded therein, precipitates from the liquid phase. The gel is then separated from the liquid phase, so that the the heat energy required for the drying of the gel can be saved. The separation of the gel from the liquid phase can be accomplished by filtration or other suitable techniques. In the case of filtration, the gel acts as a filter aid. That is, the gel prevents the filter medium from being clogged with the finely divided drug and thereby facilitates the filtration. During this separation step, the gel is preferaly maintained at or above the gelation temperature.

If it is impossible to maintain the gel at or above the gelation temperature, the gel is preferably spray-dried so as to prevent the growth or agglomeration of primary particles of the drug.

According to the above-described fourth procedure in which a solid drug that is scarcely soluble in water is pulverized in an aqueous solution of a water-soluble high-molecular substance to form an aqueous dispersion of the finely divided drug, the process of the present invention can essentially be carried out without the aid of a surface-active agent. However, a pharmaceutical composition having good wettability by water can be obtained by previously adding a very small amount of a surface-active agent to the aqueous solution of a water-soluble high-molecular substance. In the fourth procedure involving a gelation step, a pharmaceutical composition having good wettability by water can advantageously be obtained by separating the gel by filtration and then washing it with water containing a very small amount of a surface-active agent. As stated before, surface-active agents (e.g. dioctyl sodium sulfosuccinate) which hardly show the formation of micelles are preferred for this purpose. It should be noted, however, that the use of large amounts of a surface-active agent can improve the redispersibility in water of the drug but, on the other side, may impair the bioavailability thereof.

The activated pharmaceutical composition prepared by the process of the present invention exhibits a high degree of bioavailability not only when used in the form of a powder but also when made into subtle granules, granules, tablets, capsulated drug, suppository, and other pharmaceutical forms.

The present invention is further illustrated by the following examples.

EXAMPLE 1

Fifty g of sodium hydroxide was dissolved in 1.5 l of water. In this solution were dissolved 200 g of Japanese pharmacopoeial phenytoin and 20 g of hydroxypropyl cellulose (L type, manufactured and sold by Nippon Soda Co., Ltd., Japan). While the resulting aqueous solution of phenytoin, sodium hydroxide, and hydroxypropyl cellulose was being stirred vigorously, 0.5 l of water containing 100 g of citric acid was added thereto little by little so as to neutralize the solution and thereby precipitate the phenytoin. The resulting white turbid solution was heated at about 90° C. to effect gelation of the hydroxypropyl cellulose. The precipitate so formed was separated by filtration and then washed with 3 l of hot water at 80° C. or above.

Immediately after being washed, the precipitate was dried by placing it in a hot-air drying oven preheated to 110° C. so as to keep it hot. Then, the precipitate was reduced to a powder by means of a pulverizer. The phenytoin powder thus obtained was very quickly redispersed in water to form a white suspension. Using a solution obtained by adding 0.05% by weight of polysorbate 80 to the solution I for the Japanese pharmacopoeial disintegration test, the phenytoin powder prepared in this example and two commercial preparations A and B of Japanese official phenytoin were subjected to a dissolution test based on the paddle method (100 rpm, phenytoin 50 mg/l). The results thus obtained are illustrated in FIG. 1 where the curves I—I, II—II and III—III represent the activated preparation of Example 1, the commercial preparation A and the commercial preparation B, respectively.

The activated preparation of Example 1 and the commercial preparation A and B were separately administered per os to human subjects in a dose of 4 mg of phenytoin per kg of the body weight. Then, the concentration of phenytoin in the blood was periodically determined for 8 hours after administration. The results thus obtained are shown in Table 1.

In the above-described dissolution test, the commercial preparation A was slow in dissolution speed and low in dissolution rate, as illustrated in FIG. 1. Moreover, it can be seen from Table 1 that phenytoin was scarcely introduced into the blood.

Also as illustrated in FIG. 1, the commercial preparation B showed a considerable increase in blood phenytoin concentration, but with some delay.

In contrast to them, the activated preparation of Example 1 showed an increase in blood phenytoin concentration as early as an hour after administration and gave an $\bar{x}$ value of 2.12 $\mu$g/ml. Three or four hours after administration, the blood phenytoin concentration reached a maximum value of about 5 to 6 $\mu$g/ml. Thus, the activated preparation of Example 1 exhibited a remarkably high degree of bioavailability and attained an exceptionally high AUC value, as compared with the commercial preparations A and B.

EXAMPLE 2

Fifty g of sulfisoxazole was dissolved in 5 l of 0.1N hydrochloric acid. In this solution was dissolved 10 g of methyl cellulose (SM-25, manufactured and sold by Shin-Etsu Chemical Co., Ltd., Japan). While the resulting solution was being stirred, 1.0 l of 0.5N sodium hydroxide was added thereto little by little so as to precipitate the sulfisoxazole. The resulting suspension was heated at 80° C. or above to effect gelation of the methyl cellulose. The precipitate so formed was separated by filtration and then washed thoroughly with 3 l of boiling water. Thereafter, this precipitate was granulated by kneading it together with 20 g of Japanese pharmacopoeial colloidal silicon dioxide, extruding the mixture through a 40-mesh screen, and then drying the extrudate. Upon introduction into water, the dry granules thus obtained were very quickly disintegrated and redispersed in the water.

Figure 2:
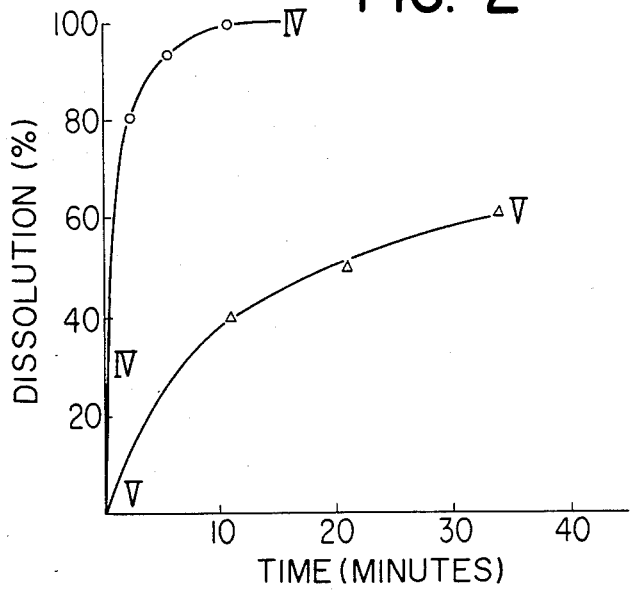
FIG. 2 is a diagram illustrating the results of the dissolution test of Example 2.

Using the solution I for the Japanese pharmacopoeial disintegration test, the dry granules prepared in this example and a commercial preparation of sulfisoxazole were subjected to a dissolution test based on the paddle method (100 rpm, sulfisoxazole 200 mg/l). The results thus obtained are illustrated in FIG. 2 where the curves IV—IV and V—V represent the activated preparation of Example 2 and the commercial preparation, respectively.

EXAMPLE 3

Ten g of nalidixic acid was dissolved in 100 ml of 1N sodium hydroxide. In this solution was dissolved 1 g of hydroxypropyl methylcellulose (60SH50, manufactured and sold by Shim-Etsu Chemical Co., Ltd., Japan). The resulting solution was neutralized with 100 ml of 1N hydrochloric acid so as to precipitate the nalidixic acid and disperse it in the water. The resulting suspension was heated at 80° C. to effect gelation of the hydroxypropyl methylcellulose. The precipitate so formed was separated by filtration, washed thoroughly with hot water at at 90° C. or above, dried in a hot-air drying oven similar to that used in Example 1, and then reduced to a powder in a mortar. The powder thus obtained was very quickly redispersed and suspended in water as well as in the solutions I and II for the Japanese pharmacopoeial disintegration test.

EXAMPLE 4

A solution of 60 g of erythromycin stearate and 15 g of Migriol ®812 (manufactured and sold by Dynamit Nobel AG., West Germany) in 200 ml of chloroform was added to a solution of 35 g of gum arabic in 100 ml of water, and this mixture was emulsified by means of Politron ® (Type PT-45, manufactured and sold by Kinematica Co., Switzerland). The resulting emulsion was dried in a spray dryer (Type F8, manufactured and sold by Freund Industrial Co., Ltd., (Japan) until the solvents were removed completely. The powder thus obtained exhibited very good redispersibility in water. When measured by means of an electron scanning microscope (Type MSM-101, manufactured and sold by Hitachi, Ltd., Japan) and the diameters of redispersed particles were within the range of 0.1 to 3.0$\mu$. (The same electron scanning microscope was used for the measurement of particle diameters in all of the following examples.)

Figure 3:
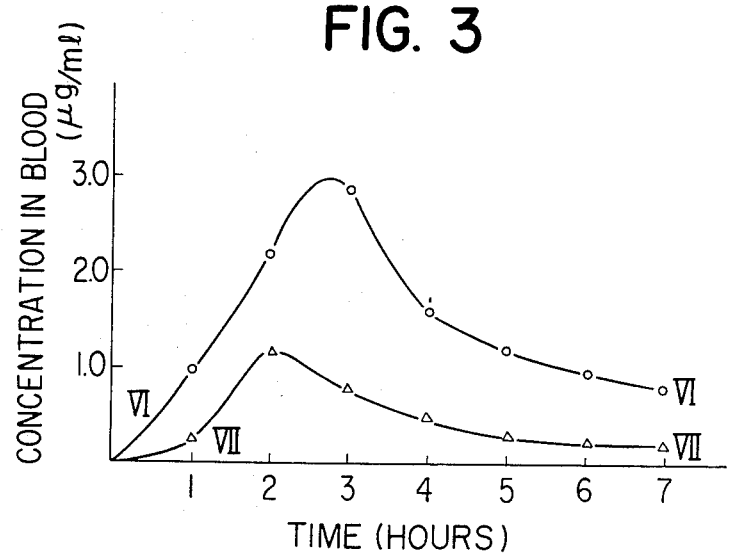
FIG. 3 is a diagram illustrating the results of the test performed on adult male human subjects in Example 4.

The erythromycin stearate powder prepared in this example and a commercial preparation A containing erythromycin stearate were separately administered per os to 6 adult male human subjects in a dose of 4 mg of erythromycin stearate per kg of the body weight. Then, the concentration of erythromycin in the blood was determined periodically. This test was of the cross-over design in which each subject received the two preparations with an interval of one week. The results thus obtained are illustrated in FIG. 3 where the curves VI—VI and VII—VII represent the activated preparation of Example 4 and the commercial preparation, respectively.

EXAMPLE 5

A solution of 5 g of ajmaline and 2 g of soybean oil in 20 ml of chloroform was added to a solution of 5 g of tragacanth gum in 20 ml of water, and this mixture was emulsified in the same manner as in Example 4. The resulting emulsion was dried in the same manner as in Example 4. The powder thus obtained exhibited very good redispersibility in water. When measured by electron microscopy, the diameters of redispersed particles were within the range of 0.5 to 2.5$\mu$.

EXAMPLE 6

A solution of 10 g of indomethacin in 50 ml of methylene chloride was added to a 50% aqueous solution of ethanol containing 5 g of hydroxypropyl cellulose (manufactured and sold by Nippon Soda Co., Ltd., Japan), and this mixture was emulsified by means of Politron ® as has been described in Example 4. In a spray dryer similar to that used in Example 4, the resulting emulsion was dried until the solvents were removed completely. The powder thus obtained exhibited very good redispersibility in water and the diameters of redispersed particles were within the range of 0.1 to 1.5$\mu$.

EXAMPLE 7

A solution of 20 g of kitasamycin in 250 ml of carbon tetrachloride was added to a solution of 10 g of gum arabic and 10 g of $\alpha$-starch in 300 ml of water, and this mixture was worked up in the same manner as in Example 4. The powder thus obtained exhibited good redispersibility in water and the diameters of redispersed particles were within the range of 0.8 to 3.5$\mu$.

EXAMPLE 8

Two g of nifedipine and 0.5 g of squalane were dissolved in 10 ml of chloroform. To this solution was added a solution of 0.5 g of gum arabic and 0.5 g of gelatin in 130 ml of water. This mixture was emulsified in the same manner as in Example 4, and the resulting emulsion was dried in a spray dryer until the chloroform and water were removed completely. The powder thus obtained good redispersibility in water and the diameters of redispersed particles were within the range of 0.1 to 3.0$\mu$.

Figure 4:
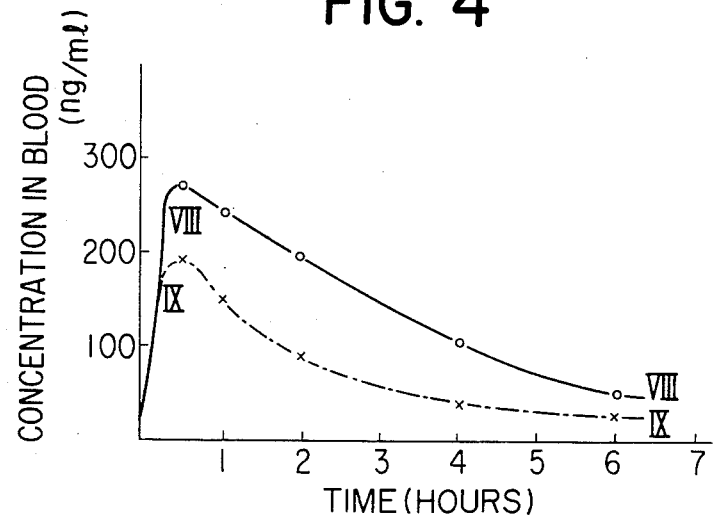
FIG. 4 is a diagram illustrating the results of the test performed on rats in Example 8.

The nifedipine powder prepared in this example and a commercially available encapsulated liquid preparation of nifedipine were separately administered per os to 4 male rats in a dose of 3 mg of nifedipine per kg of the body weight. Then, the concentration of nifedipine in the blood was determined periodically. This test was of the cross-over design in which each rat received the two preparations with an interval of one week. The results thus obtained are illustrated in FIG. 4 where the curves VIII—VIII and IX—IX represent the activated preparation of Example 8 and the commercial preparation, respectively.

EXAMPLE 9

Ten g of flufenamic acid was dissolved in 100 ml of chloroform. This solution was added to a solution of 10 g of hydroxypropyl methylcellulose (TC-5, manufactured and sold by Shin-Etsu Chemical Co., Ltd., Japan) in 100 ml of water. This mixture was emulsified in the same manner as in Example 4, and the resulting emulsion was dried in a spray dryer until the chloroform and water were removed completely. The powder thus obtained exhibited good redispersibility in water and the diameters of redispersed particles were within the range of 0.4 to 1.8$\mu$.

EXAMPLE 10

Twenty g of chloramphenicol palmitate and 10 g of Migriol ®812 (manufactured and sold by Dynamit Nobel AG., West Germany) were dissolved in 100 ml of chloroform. To this solution were added 30 ml of ethanol and 15 g of hydroxypropyl cellulose, and then 250 ml of water. This mixture was emulsified in the same manner as in Example 4, and the resulting emulsion was dried in the same manner as in Example 4. The powder thus obtained exhibited good redispersibility in water and the diameters of redispersed particles were within the range of 0.1 to 1.2$\mu$.

Figure 5:
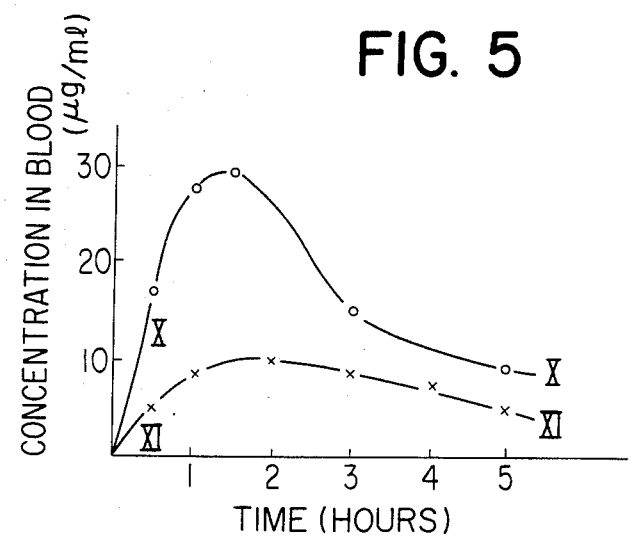
FIG. 5 is a diagram illustrating the test results of Example 10.

The chloramphenicol palmitate powder prepared in this example and a commercial preparation of chloramphenicol palmitate were separately administered per os to 4 male rats in a single dose of 250 ng (as potency) of chloramphenicol per kg of the body weight. Then, the concentration of chloramphenicol in the blood was determined periodically. The results thus obtained are illustrated in FIG. 5 where the curves X—X and XI—XI represent the activated preparation of Example 10 and the commercial preparation, respectively.

COMPARATIVE EXAMPLE 1

Instead of being dissolved in a hydrophobic organic solvent, chloramphenicol palmitate was melted and emulsified in water. The resulting emulsion was dried in a spray dryer until the water was removed completely. Then, the powder thus obtained was examined for redispersibility in water and redispersed particle size.

Specifically, 5 g of hydroxyethyl cellulose (manufactured and sold by Hercules Co., U.S.A.) and 280 ml of water were added to 20 g of chloramphenicol palmitate. This mixture was heated at 95° C. to melt and liquefy the chloramphenicol palmitate, and then emulsified by means of Politron ® operated at 20,000 rpm for 10 minutes. The resulting emulsion was dried in a spray dryer (Type F8, manufactured and sold by Freund Industrial Co., Ltd., Japan) until the water was removed completely. When introduced into water, the powder thus obtained was so poor in redispersibility that it could be dispersed only after fairly vigorous stirring. The diameters of redispersed particles were not less than 15$\mu$.

EXAMPLE 11

One hundred g of 1-isopropyl-7-methyl-4-phenyl-2(1H)quinazolinone (IMPQ) and 3 g of Migriol ®812 as has been described previously were dissolved in 250 ml of chloroform. To this solution were added 50 ml of ethanol, 40 g of methyl/cellulose (SH-25, manufactured and sold by Shin-Etsu Chemical Co., Ltd., Japan), and 400 ml of water. This mixture was emulsified in the same manner as in Example 4. The resulting emulsion was dried in a spray dryer until the chloroform, ethanol and water were removed completely. The powder thus obtained exhibited good redispersibility in water and the diameters of redispersed particles were not greater than $1\mu$.

Figure 6:
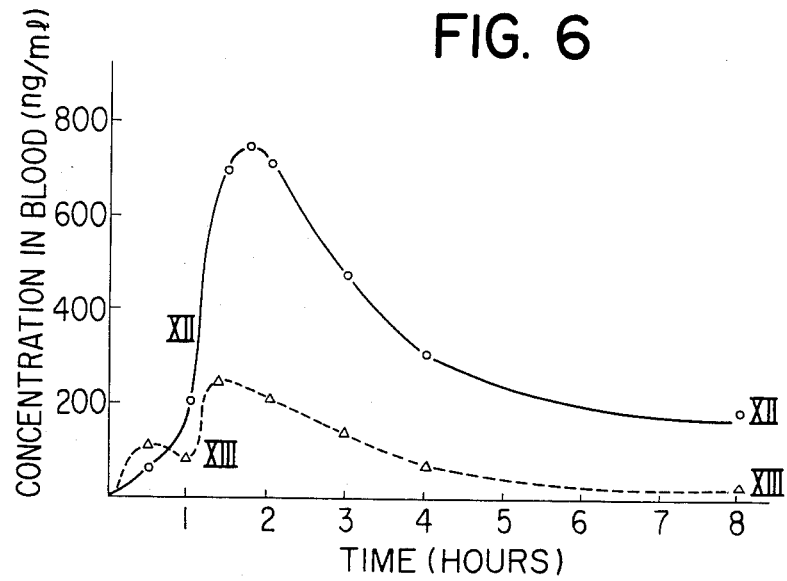
FIG. 6 is a diagram illustrating the test results of Example 11.

The IMPQ powder prepared in this example and a commercial preparation of IMPQ were separately administered per os to two groups of human subjects in a dose of 200 mg of IMPQ. Each group consisted of 7 adult men weighing an average of 61 kg. Then, the concentration of IMPQ in the blood was determined periodically. This test was of the cross-over design in which each subject received the two preparations with an interval of one week. The results thus obtained are illustrated in FIG. 6 where the curves XII—XII and XIII—XIII represent the activated preparation of Example 11 and the commercial preparation, respectively.

EXAMPLE 12

Four g of ubidecarenone was dissolved in a mixed solvent consisting of 50 ml of chloroform and 50 ml of ethanol. To this solution were added 2 g of hydroxypropyl cellulose (Type L, manufactured and sold by Nippon Soda Co., Ltd., Japan) and then 100 ml of water. This mixture was emulsified by means of an ultrasonic homogenizer (Model 200 Sonifier ®, manufactured and sold by Branson Sonic Power Co., U.S.A.) operated for 15 minutes. Using a fluid-bed spray granulator (Flocoater ® Mini, manufactured and sold by Freund Industrial Co., Ltd., Japan), the resulting emulsion was granulated by spraying it onto 80 g of lactose, during which the chloroform, ethanol and water were removed completely. The granules thus obtained exhibited good redispersibility in water and the diameters of redispersed particles were within the range of 0.1 to $0.5\mu$.

EXAMPLE 13

Ten g of indomethacin was dissolved in 50 g of methylene chloride. To this solution was added a solution of 5 g of hydroxypropyl cellulose (Type L, manufactured and sold by Nippon Soda Co., Ltd., Japan) in 100 ml of water. This mixture was emulsified by means of Politron ® as has been described previously. The resulting emulsion was heated up to 80° C. to distill off the methylene chloride and effect gelation of the hydroxypropyl cellulose. After 10 minutes, the gel so formed was separated from the liquid phase and then dried in an oven preheated to 105° C. The dry powder thus obtained exhibited good redispersibility in water. When measured by electron microscopy, the diameters of redispersed particles were within the range of 0.1 to $0.5\mu$.

EXAMPLE 14

Into the stainless steel pot (13 cm in diameter and 10 cm in height) of a vibration mill (manufactured and sold by Yokoyama Seisakusho, Ltd., Japan) were charged 72 g of phenytoin, 8 g of hydroxypropyl cellulose (HPC-L, manufactured and sold by Nippon Soda Co., Ltd., Japan). and 100 ml of water. Then, the phenytoin was wet-ground by operating the mill for 60 minutes. The resulting dispersion was transferred to a beaker and heated at 80°–90° C. to effect gelation of the hydroxypropyl cellulose. The precipitate so formed was separated from the liquid phase by filtering the dispersion while being kept at that temperature. Thereafter, the precipitate was dried in a hot-air drying oven preheated to 105° C. and then reduced to a powder by means of an atomizer (manufactured and sold by Fuji Powdal Co., Ltd., Japan). The powder thus obtained exhibited very good redispersibility in water. When measured by electron microscopy, the diameters of redispersed particles were within the range of 0.5 to $5\mu$.

Figure 7:
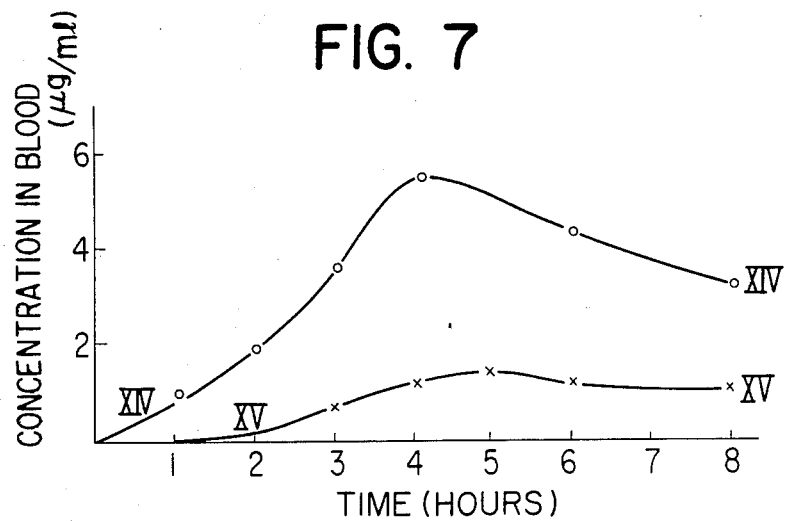
FIG. 7 is a diagram illustrating the test results of Example 14.

The hydroxypropyl cellulose-coated phenytoin powder prepared in this example and a commercial preparation of crystalline phenytoin powder were separately administered per os to 6 adult male human subjects in a dose of 4 mg of phenytoin per kg of the body weight. This test was of the cross-over design in which each subject received the two preparations with an interval of one week. The results thus obtained are illustrated in FIG. 7 where the time (in hours) elapsed after administration is plotted as abscissa and the concentration (in $\mu$g/ml) of phenytoin in the blood as ordinate. In this figure, the curves XIV—XIV and XV—XV represent the activated preparation of Example 14 and the commercial preparation, respecitvely.

EXAMPLE 15

Into a 300-ml beaker of the ordinary type were charged 32 g of phenacetin, 8 g of hydroxypropyl methylcellulose, and 200 ml of water. Then, 200 g of hard glass beads having diameters of 2 to 5 mm were added thereto. Within this beaker, a stainless steel disc (5 cm in diameter and 3 mm in thickness) was positioned 3 cm above the bottom of the beaker and a vertical shaft (3 mm in diameter) was attached to the center of the upper surface of the disc. Using an electric motor, the disc was rotated at 400 rpm for 90 minutes to wet-grind the phenacetin. The resulting dispersion was separated from the glass beads by passing it through a 30-mesh screen. After the addition of 40 g of Aerosil (manufactured and sold by Nippon Aerosil Co., Ltd., Japan), this mixture was agitated so as to allow the Aerosil to adsorb the water and thereby form wet granules. These granules were dried for 60 minutes in a hot-air drying oven kept at 80°–90° C., and the size thereof was then adjusted by forcing them through a 30-mesh screen under manual pressure.

Figure 8:
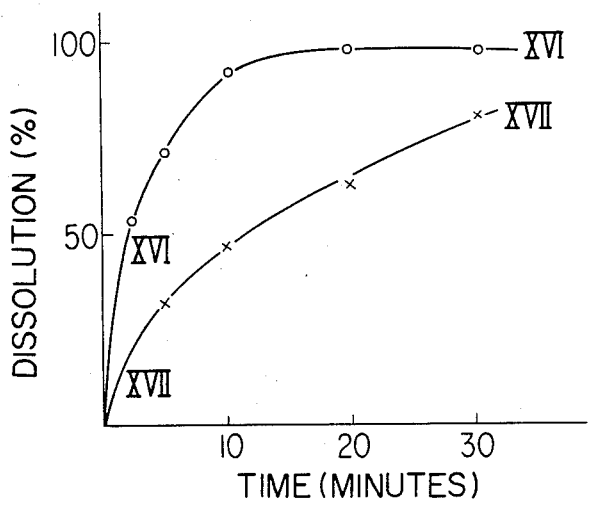
FIG. 8 is a diagram illustrating the test results of Example 15.

Using an apparatus for the U.S. pharmacopoeial dissolution tester(basket type, manufactured and sold by Toyama Kagaku Sangyo K.K., Japan), 1 g (500 mg as phenacetin) of the granules of hydroxypropyl methylcellulose-coated phenacetin powder prepared in this example was tested for dissolution rate. On the other hand, 500 mg of a commercial preparation of crystalline phenacetin was tested similarly. The results thus obtained are illustrated in FIG. 8, where the elapsed time (in minutes) is plotted as abscissa and the dissolution rate (in %) as ordinate.

TABLE 1

Blood Phenytoin Concentrations (in μg/ml) after Oral Administration of Commercial Phenytoin Preparations and Activated Phenytoin Preparation

| subject | Commercial Preparation A | | | | | | Commercial Preparation B | | | | | Activated Preparation of the Present Invention (Example 1) | | | | | |
|---|---|---|---|---|---|---|---|---|---|---|---|---|---|---|---|---|---|
| Time (hr) | | | | | | | | | | | | | | | | | |
| | 1 | 2 | 3 | 4 | 0 | 8 | 2 | 3 | 4 | 6 | 8 | 1 | 2 | 3 | 4 | 6 | 8 |
| 1 | 0 | 0 | 0 | 0 | 0 | 0 | 0 | 0 | 0 | 1.7 | 1.7 | 1.7 | 1.8 | 4.8 | 4.6 | 5.0 | 4.9 | 4.2 |
| 2 | 0 | 0 | 0 | 0 | 0 | 0 | 0 | 0 | 1.6 | 1.7 | 1.8 | 1.7 | <1 | 2.8 | 3.6 | 5.5 | 4.3 | 4.4 |
| 3 | 0 | 0 | 0 | 0 | 0 | 0 | 0 | 0 | 0 | 0 | 1.5 | 1.6 | 2.2 | 4.7 | 5.9 | 6.1 | 5.5 | 5.5 |
| 4 | 0 | 0 | 0 | 0 | 0 | 0 | 0 | 0 | 0 | 1.6 | 2.0 | 2.2 | 2.6 | 4.6 | 6.4 | 6.4 | 5.5 | 5.5 |
| 5 | 0 | 0 | 0 | 0 | 0 | 0 | 0 | 0 | 0 | 1.3 | 1.7 | 1.8 | <1 | 4.4 | 5.8 | 6.0 | 5.2 | 5.1 |
| 6 | 0 | 0 | 0 | 0 | 0 | 0 | 0 | 0 | 1.3 | 1.7 | 1.6 | 1.7 | 2.8 | 4.5 | 5.4 | 6.0 | 5.8 | 4.5 |
| 7 | 0 | 0 | 0 | 0 | 0 | 0 | 0 | 0 | 0 | 1.2 | 1.8 | 2.5 | 1.2 | 4.2 | 5.0 | 5.5 | 4.7 | 4.0 |
| 8 | 0 | 0 | 0 | 0 | 0 | 1.0 | 0 | 0 | 0 | 1.4 | 1.9 | 3.3 | | | | | | |
| 9 | | | | | | 0.1 | | | 0.4 | 1.3 | 1.8 | 2.1 | 2.12 | 4.29 | 5.24 | 5.79 | 5.13 | 4.74 |

In this figure, the curves XVI—XVI and XVII—XVII represent the activated preparation of Example 15 and the commercial preparation, respectively.

EXAMPLE 16

In a beaker were placed 160 g of chloramphenicol palmitate, 40 g of hydroxypropyl cellulose (manufactured and sold by Nippon Soda Co., Ltd., Japan) 0.16 g of dioctyl sodium sulfosuccinate, and 1,000 ml of ethanol. Then, the chloramphenicol palmitate was wet-ground for 30 minutes by means of Politron ® (manufactured and sold by Kinematica GmbH, Switzerland). The resulting dispersion was dried in a spray dryer (Type FS-20, manufactured and sold by Freund Industrial Co., Ltd., Japan). The dry powder thus obtained exhibited very good redispersibility in water.

Figure 9:
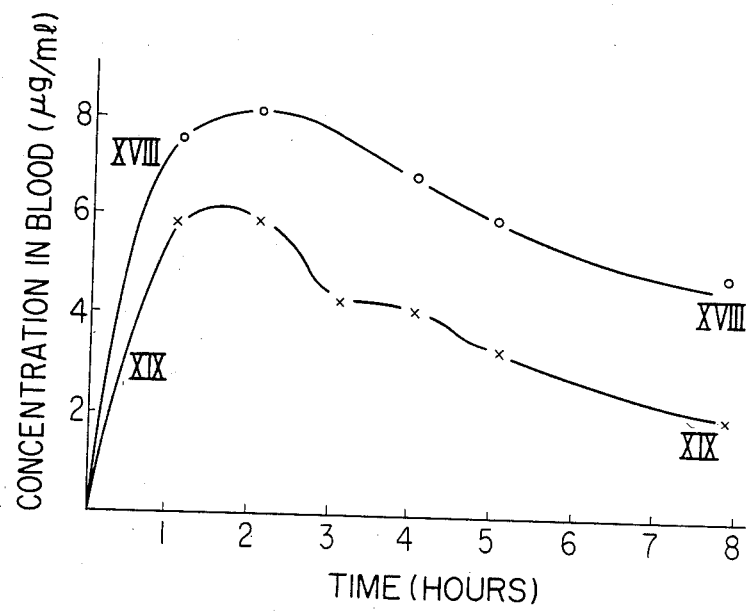
FIG. 9 is a diagram illustrating the test results of Example 16.

The hydroxypropyl cellulose-coated chloramphenicol palmitate powder prepared in this example and a commercial preparation of crystalline chloramphenicol palmitate were separately administered per os to 6 adult male human subjects in a dose of 500 mg (as potency) of chloramphenicol. This test was of the cross-over design in which each subject received the two preparations with an interval of one week. The results thus obtained are illustrated in FIG. 9 where the time (in hours) elapsed after administration is plotted an abscissa and the concentration (in μg/ml) of chloramphenicol in the blood as ordinate. In this figure, the curves XVIII—XVIII and XIX—XIX represent the activated preparation of Example 16 and the commercial preparation, respectively.

EXAMPLE 17

Into the pot of a vibration mill similar to that used in Example 14 were charged 50 g of griseoflulvin, 5 g of polyethylene glycol (6000), 5 g of methyl cellulose, and 100 ml of water. Then, the griseofulvin was wet-ground by operating the mill for 8 hours. In the same manner as in Example 14, the resulting dispersion was heated to effect gelation of the methyl cellulose. The precipitate so formed was separated from the liquid phase by filtering the dispersion while being kept at that temperature. Thereafter, the precipitate was dried in a hot-air drying oven preheated to 105° C. and then reduced to a powder by means of an atomizer (manufactured and sold by Fuji Powdal Co., Ltd., Japan). The powder thus obtained exhibited very good redispersibility in water, an artificial gastric juice, and an artificial intestinal juice. When measured by electron microscopy, the diameters of most redispersed particles were not greater than 0.5μ.

EXAMPLE 18

In a beaker were placed 30 g of hydrocortisone acetate, 10 g of ethylene oxide-propylene oxide block copolymer (Pluronic F68), 100 ml of water, and 50 ml of ethanol. Then, the hydrocortisone acetate was wet-ground for 30 minutes by means of Politron ® as has been described in Example 16. The resulting dispersion was dried in a spray dryer (Type FS-20, manufactured and sold by Freund Industrial Co., Ltd., Japan). The powder thus obtained was very quickly redispersed in water at 37° C., an artificial gastric juice, and an intestinal juice.

We claim:

1. A process for the preparation of an activated pharmaceutical composition containing a solid drug in the form of finely divided particles substantially not greater than 10 microns in diameter, which comprises the steps of:

(1) providing a solid drug that is scarcely soluble in water and is soluble in a low-boiling hydrophobic organic solvent;

(2) dissolving the solid drug in said low-boiling hydrophobic organic solvent;

(3) emulsifying the resulting solution in water in the presence of a water-soluble, high-molecular weight substance selected from the group consisting of hydroxypropyl cellulose, methyl cellulose, hydroxyethyl cellulose, hydroxypropyl methyl cellulose, hydroxypropyl ethyl cellulose, carboxymethyl cellulose sodium salt, alpha-starch, hydroxypropyl starch, pullalan, gum arabic, tragacanth gum, gelatin, polyvinyl alcohol, polyvinyl pyrrolidone and mixtures thereof; and (4) then removing the dispersion medium from the so-formed disperse system.

2. A process for the preparation of an activated pharmaceutical composition containing a solid drug in the form of finely divided particles substantially not greater than 10 microns in diameter, which comprises the steps of:

(1) providing a solid drug that is scarcely soluble in water and is soluble in a low-boiling hydrophobic organic solvent selected from the group consisting of chloroform, methylene chloride, trichloroethylene, trichloroethane, carbon tetrachloride, benzine, n-hexane, benzene, toluene, ethyl ether, isopropyl ether, methyl ethyl ketone, ethyl acetate and mixtures thereof;

(2) dissolving the solid drug in said low-boiling hydrophobic organic solvent;

(3) emulsifying the resulting solution in water in the presence of a water-soluble, high-molecular weight substance selected from the group consisting of hydroxypropyl cellulose, methyl cellulose, hyroxyethyl cellulose, hydroxypropyl methyl cellulose, hydroxypropyl ethyl cellulose, carboxymethyl cellulose sodium salt, alpha-starch, hydroxypropyl starch, pullalan, gum arabic, tragacanth gum, gelatin, polyvinyl alcohol, polyvinyl pyrrolidone and mixtures thereof; and (4) then removing the dispersion medium from the so-formed disperse system.

3. A process for the preparation of an activated pharmaceutical composition containing a solid drug in the form of finely divided particles substantially not greater than 10 microns in diameter, which comprises the steps of:

(1) providing a solid drug that is scarcely soluble in water and is soluble in a hydrophobic organic solvent which is a mixture of a low-boiling hydrophobic organic solvent and a non-volatile hydrophobic organic solvent;

(2) dissolving the solid drug in said mixture of hydrophobic organic solvents;

(3) emulsifying the resulting solution in water in the presence of a water-soluble, high-molecular weight substance selected from the group consisting of hydroxypropyl cellulose, methyl cellulose, hydroxyethyl cellulose, hydroxypropyl methyl cellulose, hydroxypropyl ethyl cellulose, carboxymethyl cellulose sodium salt, alpha-starch, hydroxypropyl starch, pullalan, gum arabic, tragacanth gum, gelatin, polyvinyl alcohol, polyvinyl pyrrolidone and mixtures thereof; and (4) then removing the dispersion medium from the so-formed disperse system.

4. A process for the preparation of an activated pharmaceutical composition containing a solid drug in the form of finely divided particles substantially not greater than 10 microns in diameter, which comprises the steps of:

(1) providing a solid drug that is scarcely soluble in water and is soluble in a hydrophobic organic solvent which is a mixture of a low-boiling hydrophobic organic solvent selected from the group consisting of chloroform, methylene chloride, trichloroethylene, trichloroethane, carbon tetrachloride, benzine, n-hexane, benzene, toluene, ethyl ether, isopropyl ether, methyl ethyl ketone and ethyl acetate and a non-volatile hydrophobic organic solvent selected from the group consisting of glycerides, liquid paraffin, squalane, squalene, lecithin, pristane, low-HLB sorbitan fatty acid esters and low-HLB sucrose fatty acid esters;

(2) dissolving the solid drug in said mixture of hydrophobic organic solvents;

(3) emulsifying the resulting solution in water in the presence of a water-soluble, high-molecular substance selected from the group consisting of hydroxypropyl cellulose, methyl cellulose, hydroxyethyl cellulose, hydroxypropyl methyl cellulose, hydroxypropyl ethyl cellulose, carboxymethyl cellulose sodium salt, alpha-starch, hydroxypropyl starch, pullalan, gum arabic, tragacanth gum, gelatin, polyvinyl alcohol, polyvinyl pyrrolidone and mixtures thereof; and (4) then removing the dispersion medium from the so-formed disperse system.

5. The process according to claim 1, 2, 3 or 4, wherein the water-soluble, high-molecular substance is dissolved in water before emulsification.

6. The process according to claim 1, 2, 3 or 4, wherein the solid drug that is scarcely soluble in water and is soluble in a hydrophobic organic solvent is selected from the group consiting of ajmaline, isopropyl antipyrine, quinine ethylsulphate, ethenzamide, erythromycin, erthyromycin fatty acid ester, kitasamycin, chlorpropamide, chlormezanone, cortisone acetate, diazepam, digitoxin, cyclophosphamide, spironolactone, nalidixic acid, amobarbital, indomethacin, jasamycin, nifedipine, ubidecarenone and chloramphenicol palmitate.

7. The process according to claim 1, 2, 3 or 4, wherein the step of removing the dispersion medium from the disperse system is carried out by evaporation as rapidly as possible.

8. The process according to claim 1, 2, 3 or 4, wherein the step of removing the dispersion medium from the disperse system is carried out by spray-drying the disperse system.

9. The process according to claim 1, 2, 3 or 4, wherein the step of removing the dispersion medium from the disperse system is carried out by spraying the disperse system onto an excipient in a fluid-bed spray granulator.

10. The process according to claim 1, 2, 3 or 4, wherein after removal of the dispersion medium, further comprises the step of forming the resulting activated pharmaceutical composition into subtle granules, granules, tablets, sugar-coated tablets or suppositories.

* * * * *